US006842010B2

(12) United States Patent  
Biernacki

(10) Patent No.: US 6,842,010 B2
(45) Date of Patent: Jan. 11, 2005

(54) METHOD AND APPARATUS TO EVALUATE DIELECTRICALLY-ANISOTROPIC MATERIALS USING ANALYSIS OF MULTIPLE MICROWAVE SIGNALS IN DIFFERENT PLANES OF POLARIZATION

(75) Inventor: Jacek M. Biernacki, Salmon Arm (CA)

(73) Assignee: Precarn Incorporated, Ottawa (CA)

( * ) Notice: Subject to any disclaimer, the term of this patent is extended or adjusted under 35 U.S.C. 154(b) by 14 days.

(21) Appl. No.: 10/158,152

(22) Filed: May 31, 2002

(65) Prior Publication Data

US 2003/0222657 A1 Dec. 4, 2003

(51) Int. Cl.[7] .............................................. G01R 27/32
(52) U.S. Cl. ...................................................... 324/637
(58) Field of Search ............................... 324/637, 639, 324/76.11–76.21, 631

(56) References Cited

U.S. PATENT DOCUMENTS

| | | |
|---|---|---|
| 4,500,835 A | 2/1985 | Heikkila |
| 4,514,680 A | 4/1985 | Heikkila et al. |
| 4,941,357 A | 7/1990 | Schajer |
| 5,619,143 A | 4/1997 | Stevens et al. |
| 6,293,152 B1 * | 9/2001 | Stanish et al. ................. 73/597 |
| 6,510,734 B1 * | 1/2003 | Feller ........................... 73/160 |

OTHER PUBLICATIONS

Built Environment Innovation & Construction Technology, No. 19, New Electronic Timber Grading—by Microwave, Press Release Jun. 8, 2001; Ref: 2001/142.

* cited by examiner

Primary Examiner—N. Le
Assistant Examiner—Amy He
(74) Attorney, Agent, or Firm—Antony C. Edwards

(57) ABSTRACT

An apparatus for evaluating dielectrically-artisotropic materials comprising a plurality of microwave transmitters with more than two planes of polarization, and a plurality of microwave receivers with differing planes of polarization, wherein each transmitter includes a modulator modulating the transmitted microwave beam, the transmitters and receivers arranged, relative to a workpiece to be measured, so as to cooperate in communication therebetween, and wherein connected to each receiver is a device to identify the received amplitude and phase of a component of the transmitted microwave beam, and wherein connected to each receiver is a processor for analyzing the received signals to take more than two measurements including measuring the principal axes, attenuations and phase shifts of the received microwave beam.

5 Claims, 10 Drawing Sheets

METHOD AND APPARATUS TO EVALUATE DIELECTRICALLY-ANISOTROPIC MATERIALS USING ANALYSIS OF MULTIPLE MICROWAVE SIGNALS IN DIFFERENT PLANES OF POLARIZATION

TECHNICAL FIELD

The invention described here is an apparatus for evaluating the physical properties of dielectrically-anisotropic materials. It was originally conceived as an industrial device for sorting lumber, and therefore the descriptions given below are presented in that context. However, it can be seen that the invention can be successfully applied in much more general contexts. Therefore, the descriptions below should be understood to exemplify just one of a wide range of potential uses.

BACKGROUND OF THE INVENTION

When using wood for industrial purposes, it is important to exercise careful quality control to ensure that the material properties are properly matched to the desired end uses. However, wood is a natural material, and can have a wide range of mechanical properties, even within a single species. Consequently, it is important to be able to sort the wood into different grades, each with specific material properties. Such sorting allows the wood resource to be used efficiently and economically.

Typical wood properties of interest include specific gravity, moisture content, grain direction, stiffness and strength. These properties are of industrial importance both individually and in combination. Perhaps the most challenging property to estimate is wood strength. This is because it is controlled in a subtle way by several different wood characteristics. Accurate identification of wood strength is essential when producing lumber that is to be used for structural applications.

The traditional method for estimating wood strength is by visual observation. The process involves human observation of wood features such a knots and grain distortions. Wood strength is then estimated from the observed features using standardized empirical rules. The visual method is subject to several uncertainties and has only modest strength estimation capabilities.

The bending method is the most common mechanical process for estimating wood strength. The procedure involves bending the wood and measuring the force required to produce a given deflection. The bending method gives a better estimate of wood strength than visual grading, but the estimation accuracy is still only moderate. The available accuracy is mainly limited by the coarse resolution of the stiffness measurement. This measurement is typically done over a 4 foot span, while the main strength controlling features, the knots, are only 0.5–2 inches in diameter. Additionally, a bending machine cannot measure the first and last 2 feet of a board. Bending machines also require intensive maintenance.

X-ray absorption provides a more accurate method of wood strength grading. Schajer describes the method in U.S. Pat. No. 4,941,357 entitled "Method and Apparatus for Estimating the Strength of Wood." The procedure uses X-ray absorption to indicate the gross density of the wood. The method has fine resolution, comparable to, or finer than, the size of the knots. The X-ray measurements extend from end to end of each board, and so all the material is examined. In addition, the measurements are non-contact, thereby minimizing machine maintenance needs.

Recent advances in computing power have enabled more sophisticated mathematical techniques to be used for wood sorting applications. These mathematical techniques can take into account multiple factors that control wood strength and other properties. They combine the effects of these factors to achieve more accurate wood property estimates. For maximum effectiveness, the mathematical techniques need to work with large amounts of measured data. These data should preferably include measurements of several independent wood properties and they should have fine spatial resolution. The X-ray method provides measurements that partially meet this need. They have fine resolution, but however, they indicate only one wood property, bulk density.

The invention described here is a device that is capable of simultaneously providing fine-resolution of up to five independent wood dielectric properties. These dielectric properties can be used to indicate wood mechanical properties. The invention provides the large amount of fine-resolution, multi-property data that are needed to achieve superior wood strength estimates using the sophisticated mathematical techniques. The same measurements and mathematical techniques can be used to estimate other useful wood properties such as moisture content and stiffness.

PRIOR ART

Several microwave-based methods for measuring wood properties have previously been developed. Typical objectives include knot detection, and identification of wood grain direction and moisture content. The various methods involve measuring the changes in a microwave field that are caused by the presence of the wood. These measurements can be done in reflection mode, where the transmitters and receivers are on the same side of the wood specimen. Alternatively, they can be done in transmission mode, where the transmitters and receivers are on opposite sides of the wood specimen. Typical measured quantities include microwave amplitude, phase shift, resonant frequency and Q factor. A common objective in many microwave system designs is the ability to indicate a particular wood property independent of unknown variations in other wood properties.

In U.S. Pat. No. 3,810,005, Bennion et al. describe a device that identifies knots and flaws in wood by comparing the microwave attenuations measured at adjacent locations. The device is designed to identify knots independent of wood moisture content, density and angle. It therefore does not indicate these three wood properties.

In U.S. Pat. No. 4,123,702, Kinanen also describes a device for identifying knots and other flaws in wood. This device monitors the phase change of a microwave beam that transmits through the wood. The device is also designed to be independent of wood moisture content, density and grain angle, and it therefore does not indicate these three wood properties.

In U.S. Pat. No. 4,500,835, Heikkilä describes a device for identifying wood grain direction using switchable, orthogonally polarized transmitters and receivers. By comparing the attenuations measured when different combinations of transmitters and receivers are activated, the grain angle of the wood can be identified. The measurement method allows this angle to be identified independent of the moisture content and density of the wood, and the possible presence of knots. A limitation of the measurement method is that it only indicates the size of the grain angle, but not its sign. Thus, grain deviations to the left or to the right cannot be distinguished.

In U.S. Pat. No. 4,087,746, Kanae describes a method for identifying the principal directions of an orthotropic material. It involves measuring the reflection from a microwave beam whose polarization is mechanically rotated. This method is designed for laboratory measurements with individual samples. It is not well suited to on-line industrial measurements.

In U.S. Pat. No. 4,710,700, Osaki describes a method for identifying the principal directions of a paper sample by measuring resonant frequency and Q factor of a paper sample in a resonant cavity. This method is also designed for laboratory measurements with individual samples, and is not well suited to on-line industrial measurements.

In U.S. Pat. No. 5,619,143, Stevens et al. describe a device for measuring wood grain angle. The preferred embodiment uses electrically synchronized Faraday rotators to rotate and de-rotate a linearly polarized microwave beam that transmits through the wood sample. In practical applications, the described device requires careful adjustment and calibration to achieve accurate operation. The electrical alignment of the Faraday rotators must be accurately controlled over the entire range of rotation. Variations in transmitted amplitude and phase of the rotator and de-rotator over the range of rotation must also be accounted for if accurate attenuation and phase shift measurements are to be made. Faraday rotators are relatively low-speed devices that are capable of maximum rotation speeds of a few hundreds of Hz. High-speed, high-resolution applications require measurements at some thousands of Hz.

SUMMARY OF THE INVENTION

The invention described here comprises an apparatus for making microwave measurements on an anisotropic material, and a method for processing those measurements to identify the principal directions of the material, and attenuations and phase shifts of the transmitted signals. The apparatus and method are designed to provide a practical way of measuring material properties under industrial conditions, and where high speed, consistent accuracy and simultaneous measurement of several independent material properties are important.

For ease of explanation, the invention is described here in terms of a specific application referring to wood property measurement. It is to be understood that the usefulness of the invention extends beyond this example application, and that it can be applied to measurements on a wide range of anisotropic materials.

The apparatus consists of a microwave source, two or more microwave transmitters with differing planes of polarization, and two or more microwave receivers, also with differing planes of polarization. Connected to each transmitter is a means of modulating the amplitude of the transmitted microwave beam. Connected to each receiver is a means to identify the received amplitude and the phase relative to the transmitted beam. Further connected to the receivers is a means of analyzing the received amplitude and phase outputs to identify the principal direction, attenuations and phase shifts of the received microwave beam.

Two or more microwave transducers (receivers or transmitters) could be mounted sharing the same axis of symmetry or could be separated, mounted in different axes. In other words, the transmitters could be separate or coaxial, and the receivers could be separate or coaxial. The transmitters and receivers could be mounted on opposite sides of the wood sample. This would enable a transmission measurement. Alternatively, the transmitters and receivers could be mounted on the same side of the wood sample. This would enable a reflection measurement.

The transmitted microwave beams are modulated in a known way. The corresponding amplitude and phase outputs from the receivers are then analyzed to determine the dielectric properties of the part of the wood sample through which the transmitted beams passed. It is possible to modulate the transmitted microwave beams and to analyze the received beams using either analog or digital methods. In the analog method, electronic circuitry provides the modulation signal and does the signal analysis. This approach is conceptually straightforward, but the resulting circuitry is fixed and is not easy to adapt to future needs. In the digital method, a digital device such as a computer provides the modulation signals using a digital-to-analog interface. The received amplitude and phase shift outputs are read using an analog-to-digital interface. Digital control of the modulation signals and analysis of the various outputs allows great flexibility in the operation of the system. Sophisticated mathematical procedures can be used on the measured data to enhance accuracy and to minimize the effects of measurement errors. Digital control also facilitates interface with other industrial devices, which are likely also to be digital.

The method for using the invention involves first taking reference readings of the amplitude and phase shift outputs. For a transmission type measurement, this requires a clear transmission path between the transmitters and receivers, with no wood present. For a reflection type measurement, this requires insertion of a metal reflector in place of the wood. The reference readings are taken as the transmitted beams are modulated in a specified way. This measurement defines the reference amplitudes and phases. Subsequent amplitude and phase measurements with wood in place are then evaluated relative to the reference measurements. This procedure makes the microwave system self-calibrating and insensitive to variations in the gain and phase shifts of the various microwave components involved.

In many applications, it is of interest to measure the properties of the wood sample in adjacent locations. This can be done by using an apparatus with individual transmitters and receivers for each location. Another possibility is to have all locations illuminated by the same transmitters, with individual receivers for each measurement location. Yet another possibility is to have individual transmitters for each measurement location, with common receivers. All these possibilities, not intended to be limiting, form part of the present invention.

BRIEF DESCRIPTION OF THE DRAWINGS

The preferred embodiment of the invention will be described by reference to the accompanying drawings, in which.

EMBODIMENTS OF THE INVENTION

Figure 1:
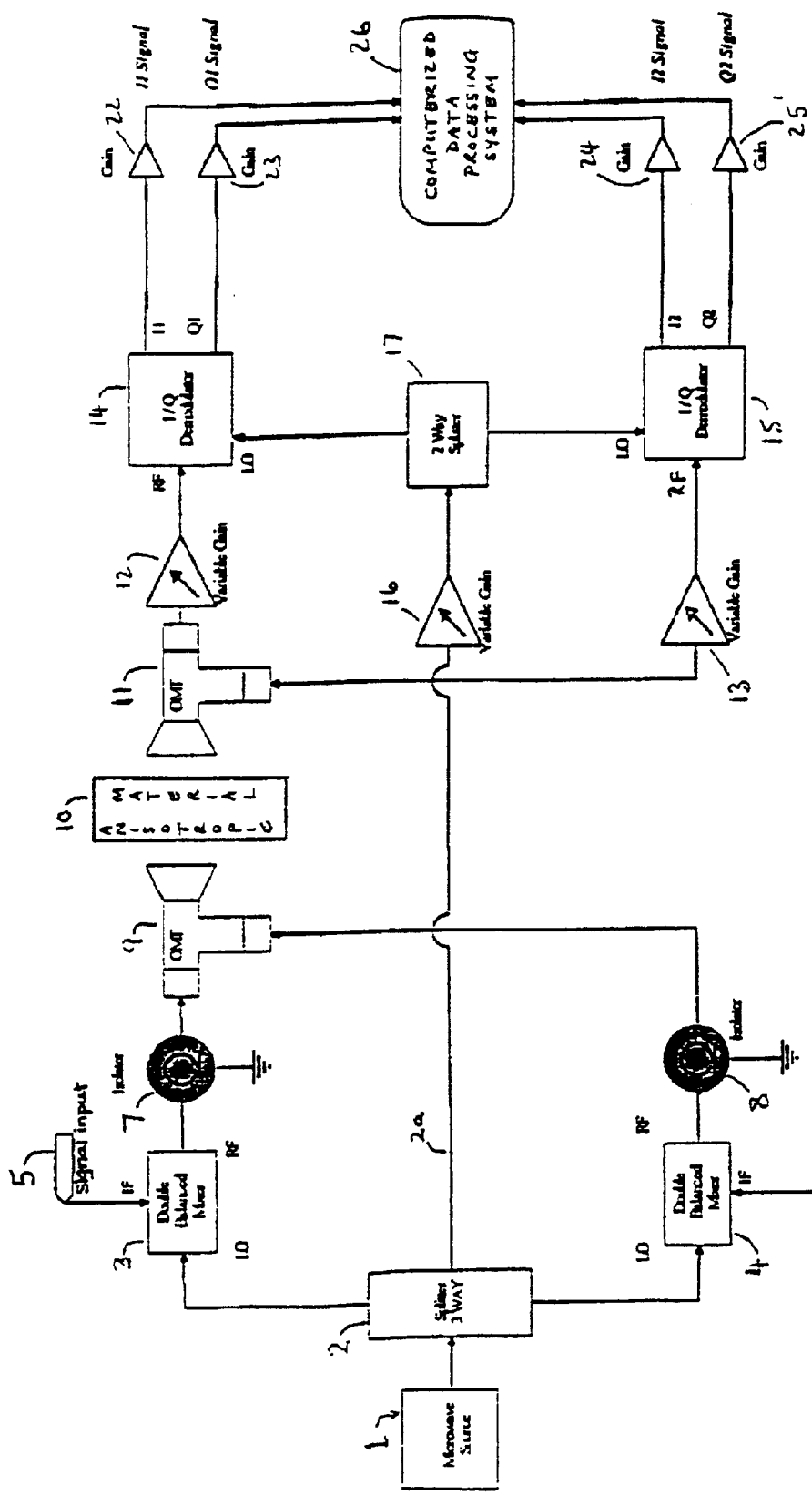
FIG. 1 is a representation of an apparatus embodying the invention that schematically shows a typical arrangement of components.
Figure 1A:
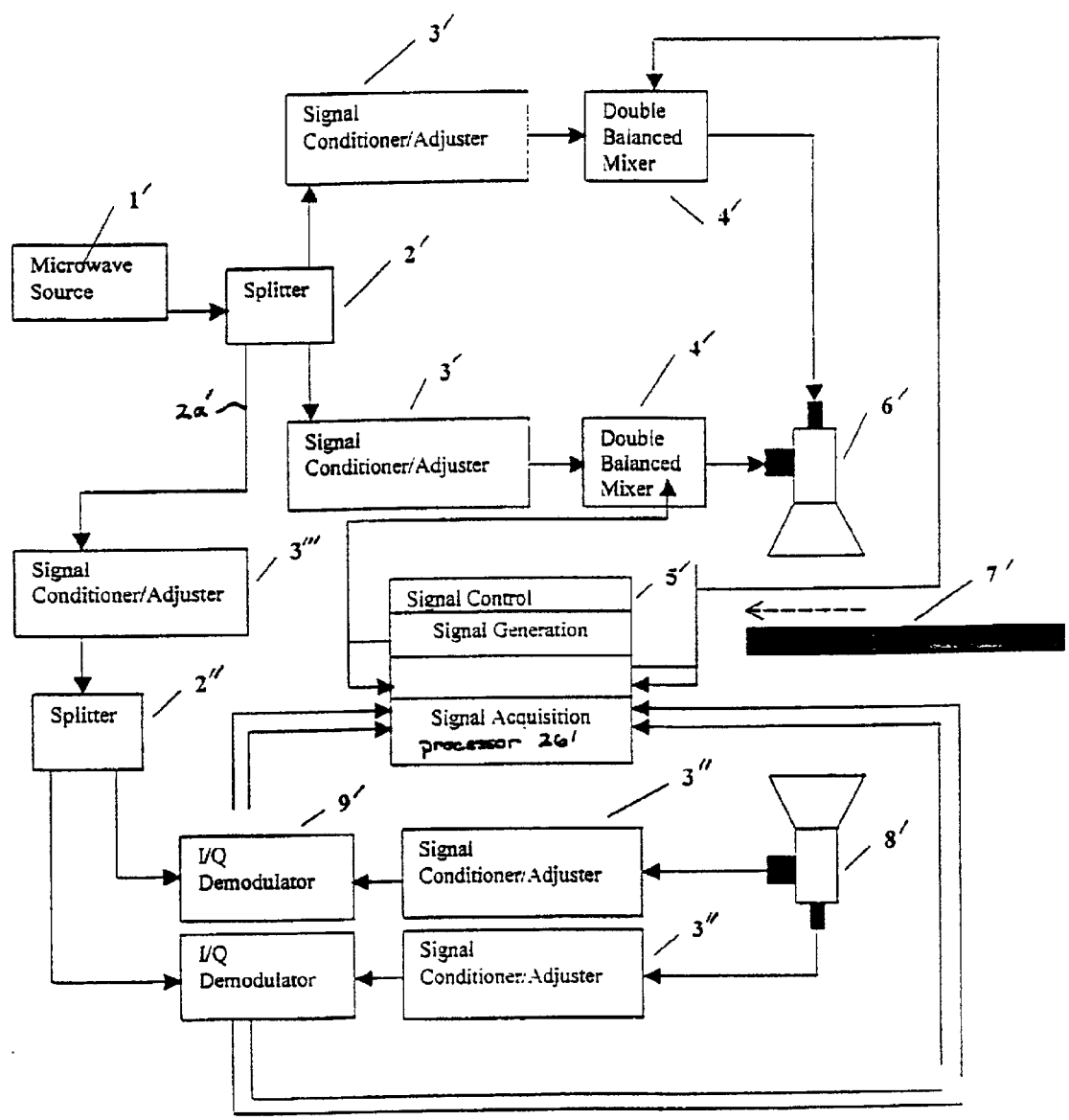
FIG. 1a is a more generic schematic characterization of the apparatus of FIG. 1.

FIGS. 1 and 1a show, respectively, a schematic diagram of one embodiment of the invention. A microwave source 1 and 1' is connected to a three-way splitter 2 and 2'. Two branches of the splitter connect to double balanced mixers, 3 and 4 in FIG. 1, and 4' in FIG. 1a, which are modulated by signal inputs 5 and 6 in FIG. 1 and 5' in FIG. 1a. The outputs from the double balanced mixers pass through isolators 7 and 8 in FIG. 1 and through signal conditioner/adjusters 3' in FIG. 1a to an orthomode transducer 9 and 6'. The orthomode transducer transmits a microwave beam towards and through the wood sample 10 and 7'. This beam comprises the two signal components with mutually orthogonal planes of polarization. In general, this beam is elliptically polarized. There is no need, nor any effort made, to synchronize the phases of the two orthogonal components.

A second orthomode transducer 11 and 8' at the other side of the wood receives the orthogonal components of the microwave signal that has passed through the wood. The two orthomode transducers are aligned coaxially and with the same planes of polarization. The received signals pass through amplifiers 12 and 13 in FIG. 1 and through signal conditioner/adjusters 3" in FIG. 1a to I/Q demodulators 14 and 15 in FIG. 1 and 9' in FIG. 1a. The two I/Q demodulators are referenced to the microwave source 1 and 1' through a third branch 2a and 2a' of the three-way splitter 2 and 2', an amplifier 16 in FIG. 1 and signal conditioner/adjuster 3''' in FIG. 1a and a two-way splitter 17 and 2". The I/Q demodulators each provide outputs corresponding to the components of the received microwave beam components in phase and in quadrature with the microwave source. In FIG. 1 these outputs pass through amplifiers 22, 23, 24 and 25 to a computer system 26, and in FIG. 1a to a signal acquisition processor 26'. The computer system and processor analyzes the outputs and evaluates their amplitudes and phases, and provides the signals 5 and 6 to the double balanced mixers 3 and 4. With respect to FIG. 1a, which is intended to illustrate a more generic schematic than that of FIG. 1, it is understood that, without intending to be limiting, signal conditioner/adjusters 3', 3" and 3''' may include one or more of the following: a filter, an amplifier, a phase shifter, an attenuator, and an isolator.

The measurement procedure involves first taking reference readings of I/Q outputs with no wood present between the transmitters and receivers. The two component microwave beams are modulated using a periodic function, f(ωt), square wave for example. The I/Q outputs are measured at least four times at equal time intervals within one cycle of the modulation. Measuring the I/Q outputs more than four times over one modulation cycle is desirable because this practice reduces the effects of random measurement errors. Measurements over multiple modulation cycles can also be helpful.

Subsequent similar measurements of the I/Q outputs with wood in place are then evaluated by the computer system. The computer system compares the new measurements with the reference measurements, and uses a mathematical algorithm to evaluate the principal direction and the principal attenuations and phase shifts. These principal quantities correspond to the wood grain direction and the attenuations and phase shifts parallel and perpendicular to the wood grain. The double-measurement procedure without and with wood makes the microwave system self-calibrating and eliminates the need for sensitive adjustment or control of the transmitted beam amplitudes or phases.

Figure 4:
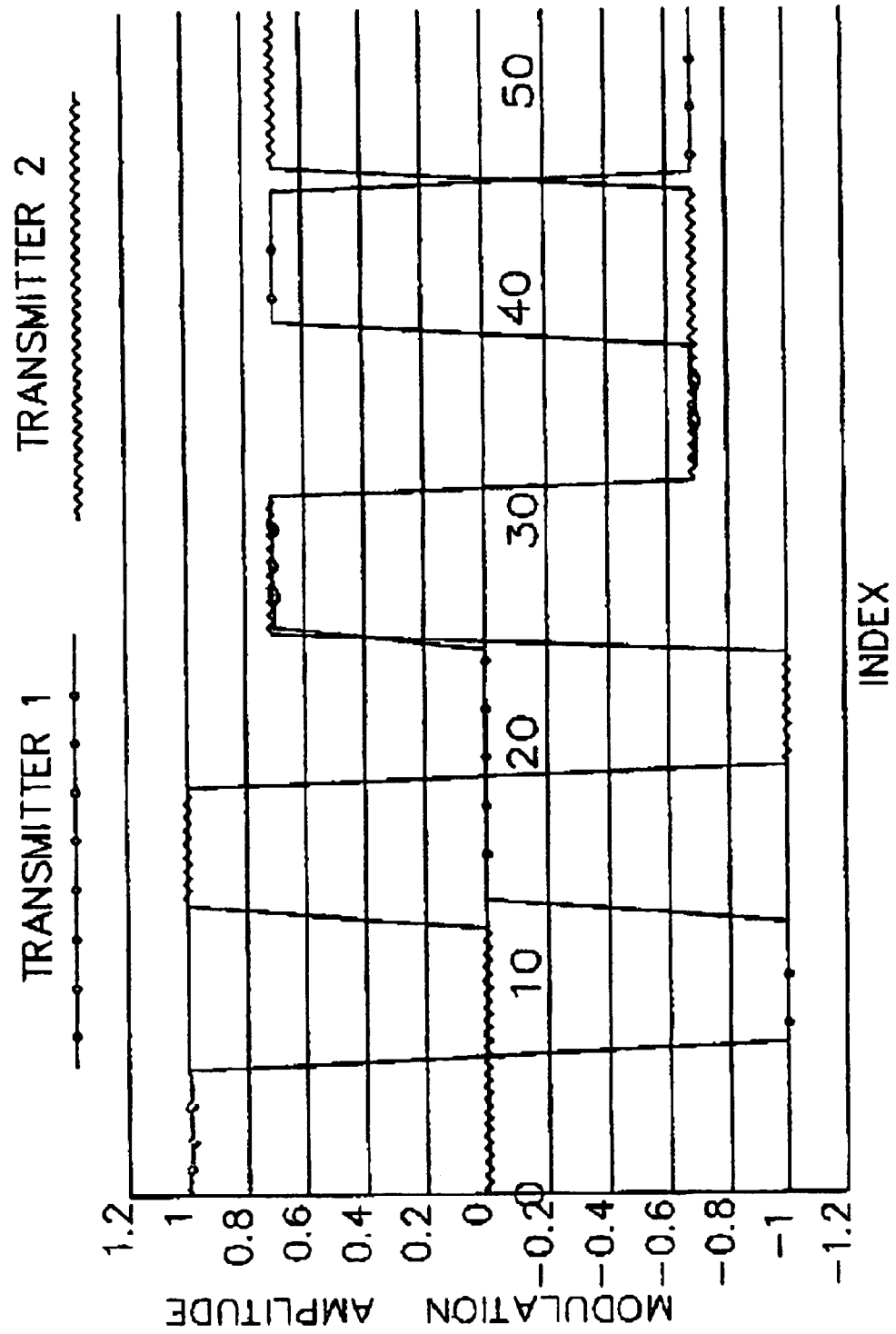
FIG. 4 illustrates an example of alternative signal modulation.

The transmitters may be a pair of orthogonal transmitters modulated by modulating means for modulating using any two periodic functions, f(t) for a first transmitter of said transmitters and $+/-(1-(f(t))^2)^{1/2}$ for a second transmitter of said pair of orthogonal transmitters. FIG. 4 shows an example one period of such modulation signals.

Figure 5A:
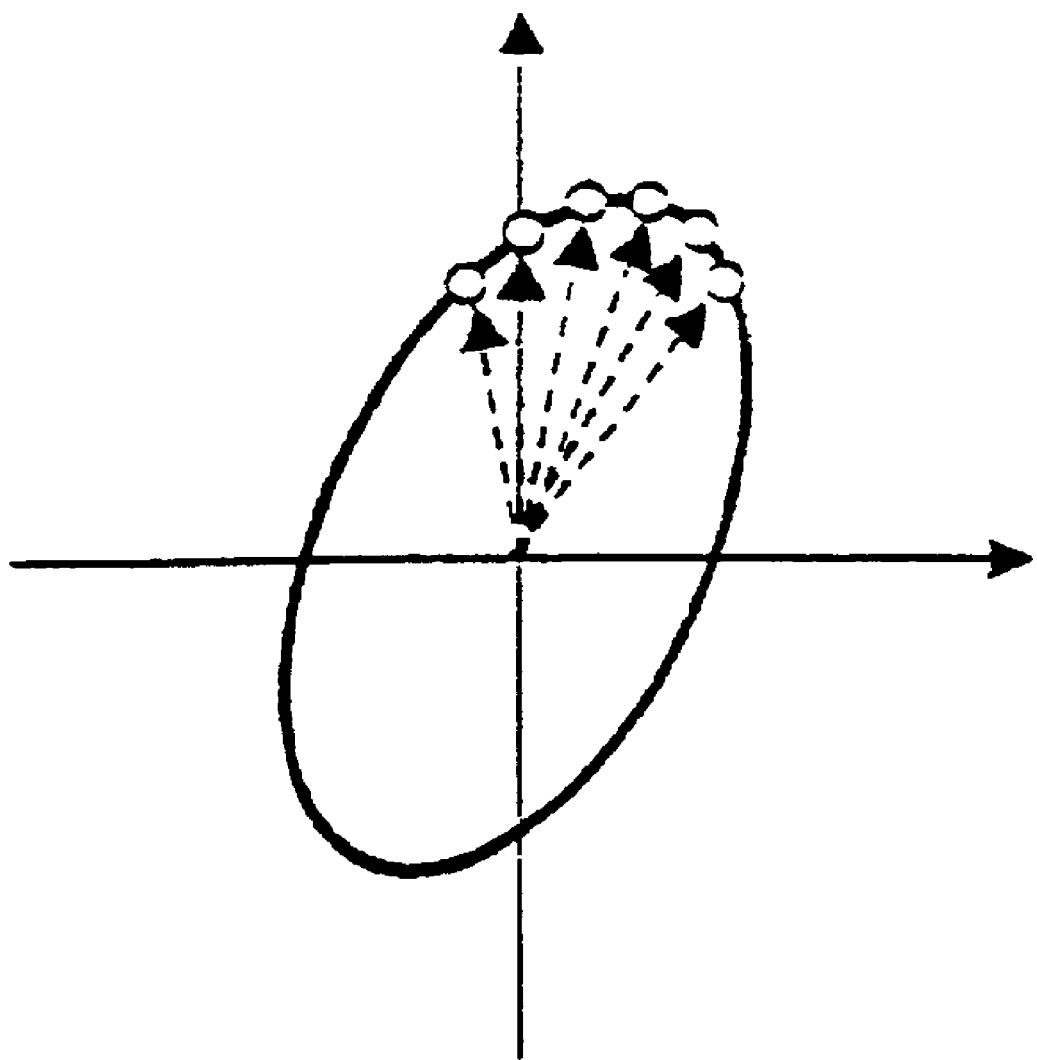
FIG. 5a diagrammatically illustrates a signal for modulating a transmitter where the signal corresponds to a nominal grain direction.

The transmitter may be modulated by a signal corresponding to a nominal grain direction such as seen in FIG. 5a. This allows for higher processing speed and better accuracy of grain angle detection close to zero. Accurate detection of small angles is important for lumber products because most contain a small average grain angle, approximately +/-2 degrees.

Figure 5B:
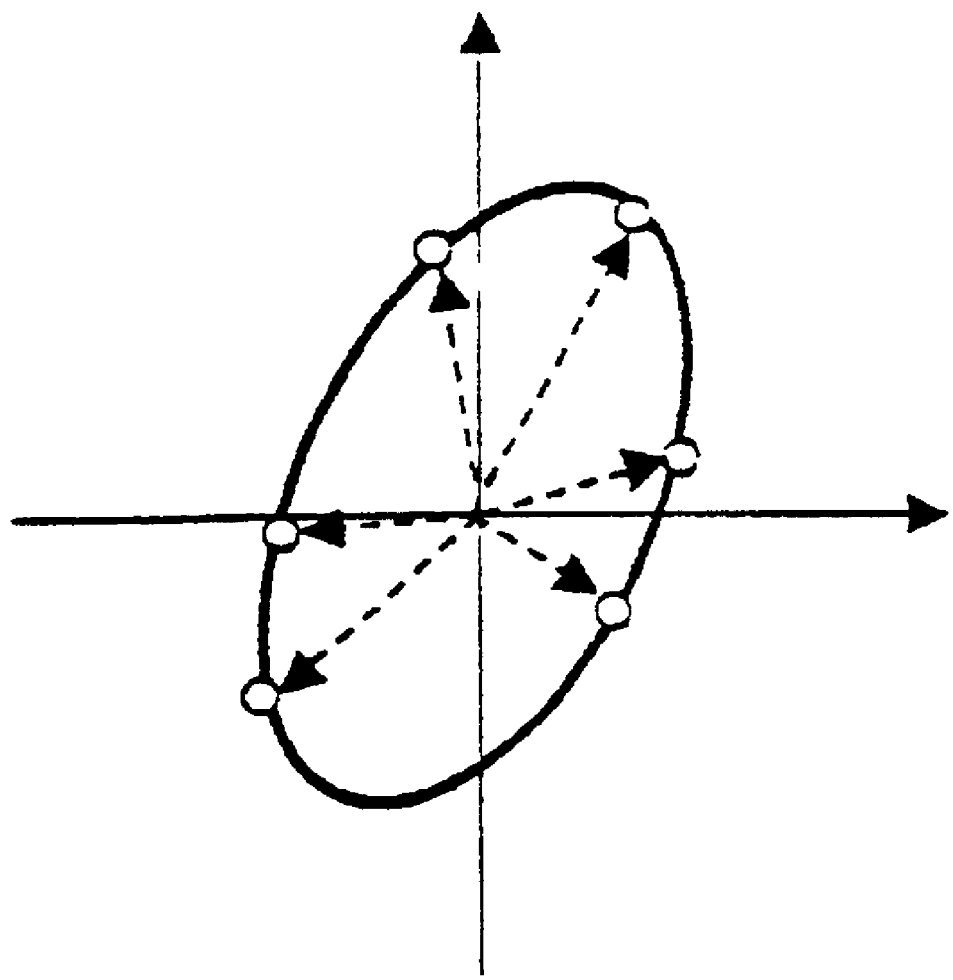
FIG. 5b diagrammatically illustrates a signal for modulating a transmitter where the signal is in random directions.

The transmitter may also be modulated by a signal in random directions and equal amplitudes and seen in FIG. 5b.

Figure 6:
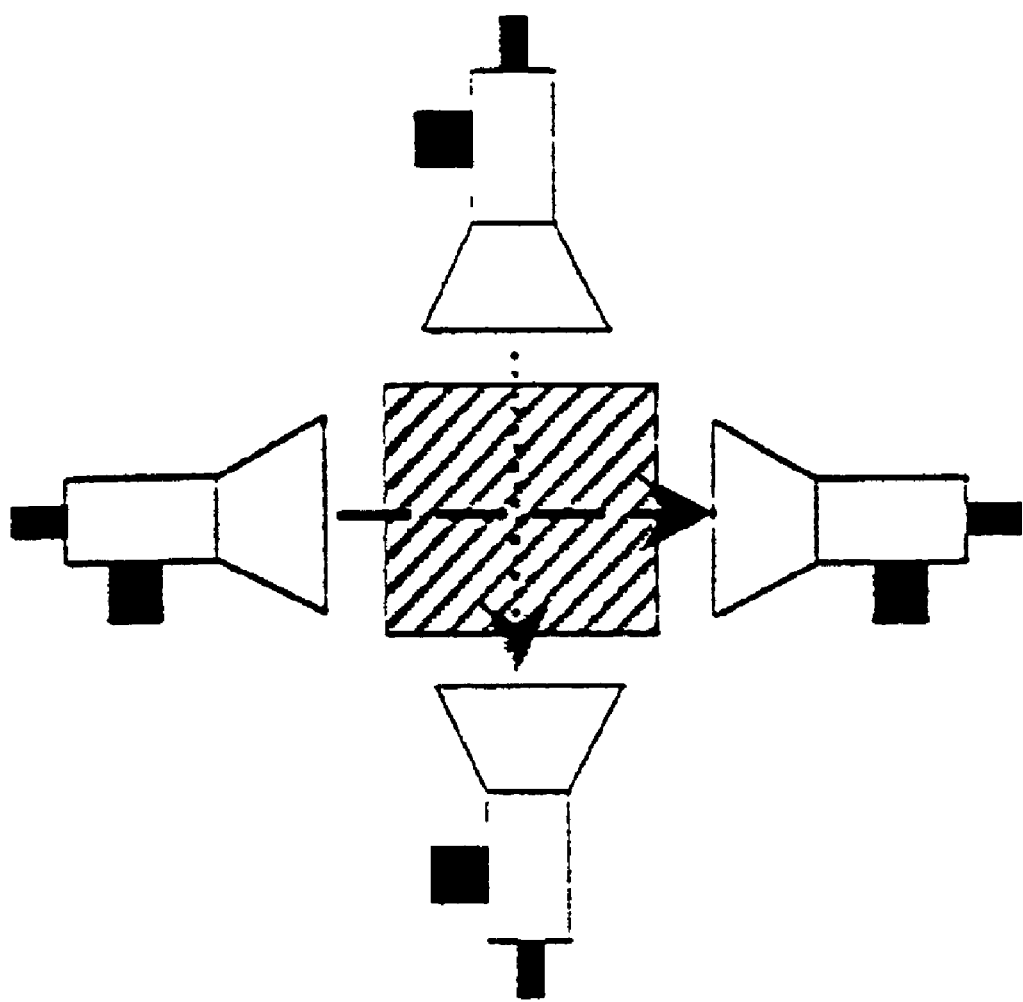
FIGS. 6 and 7 illustrate scanning directions with respect to a scanning material cross-section, symmetrical and non-symmetrical to the scanning object planes of symmetry.
Figure 7:
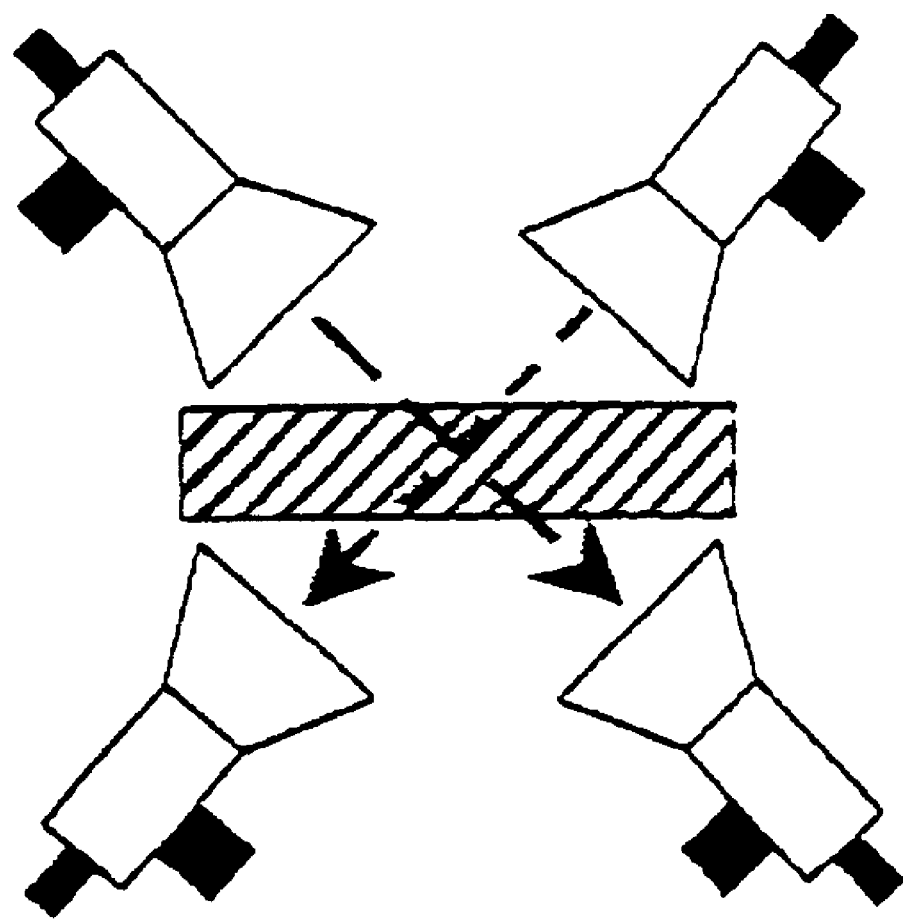

The apparatus according to the present invention may consist of more than one scanning direction with respect to the scanned object. Each scanning direction may consist of a multi-planar transmitter/receiver set independently allowing assessing material principle directions, such as grain angle in two dimensions. Signals from both transmitter/receiver sets are then combined using a simple geometry to recreate 3-dimensional principle directions. This allows detecting "diving grain" in lumber. FIGS. 6 and 7 show possible scanning directions in respect to a scanning material cross-section, symmetrical and non-symmetrical to the scanning object planes of symmetry. The scanning directions may be orthogonal.

Both the transmitter modulation and receiver signals may be acquired asynchronously with respect to the transmitter modulation periods. Synchronization is achieved by computing at the beginning of the period of the transmitter modulation signal and using this information to adjust phase of the transmitter signal. This method allows even spatial sampling of an object as it passes through the scanner. Other adjustments include adjusting microwave measurements to account for the temperature of the scanned object. Phase measurements may be adjusted using amplitude measurements. Microwave phase measurements are computed based on the I/Q demodulators signals in a limited range, typically 0 to 360 degrees, and are adjusted to cover a greater range using a relationship between phase and amplitude. The phase and amplitude relationship is being obtained for a specific material. Amplitude measurements are adjusted to non-linear response of the components (as in the flow chart). I/Q Demodulators may be replaced by power detectors.

The microwave measurements may be combined with material density information to compute a moisture content prediction, where the material density information may be obtained using X-rays.

Figure 2:
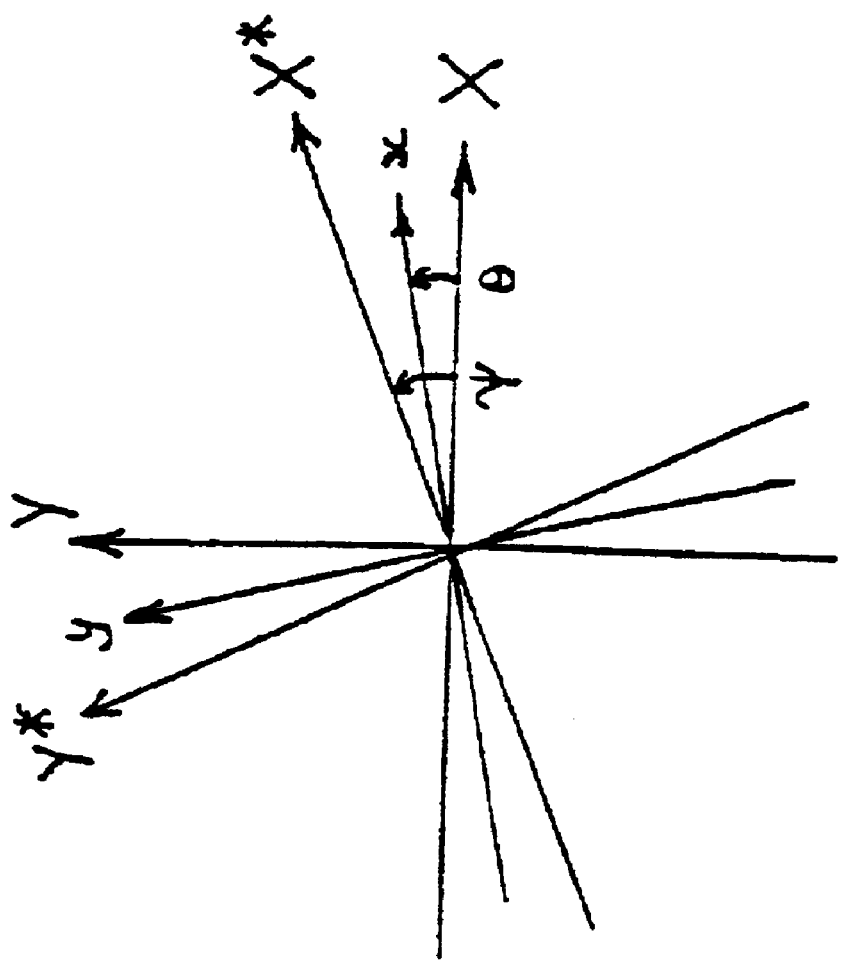
FIG. 2 shows the relationships among the axial directions of the orthogonal transmitters and receivers and the wood grain direction.

FIG. 2 shows three sets of concentric orthogonal axes. Axes X and Y lie in the polarization directions of the receiving orthomode transducer 11 in FIG. 1. Axes X* and Y* lie in the polarization directions of the transmitting orthomode transducer 9. Axes x and y lie in the directions parallel and perpendicular to the grain of the wood sample 10. Angle θ is the wood grain angle measured from the receiver axes, and angle Ψ is the misalignment angle between the transmitter and receiver axes.

When a microwave beam transmits through an anisotropic material such as wood, attenuation and phase change of the beam occurs. These effects can be characterized by two constants u and v representing the complex attenuation of the components of the microwave beam that are parallel and perpendicular to the wood grain. In an Argand diagram, the magnitudes of u and v represent the microwave attenuation parallel and perpendicular to the wood grain. The angles of u and v represent the corresponding phase changes.

Let A and B represent the complex amplitudes of the transmitted microwave beam components in directions X*, Y*. In an Argand diagram, the magnitudes and angles of these two quantities represent the microwave beam amplitudes and phases in the two orthogonal directions. The computer system 26 in FIG. 1 provides signals 5 and 6 to the double balanced mixers 3 and 4, thereby modulating the transmitted beam from the orthomode transducer 9.

Let $E_1$, $E_2$, $E_3$ and $E_4$ be the means of $D_x$ within the four quadrants of one modulation cycle. Let $F_1$, $F_2$, $F_3$ and $F_4$ be the corresponding means of $D_y$. These means mathematically correspond to the integrals of $D_x$ and $D_y$ over the various quadrants divided by the integration interval. It may be shown that:

$$C_X = \frac{\pi}{16}(E_1 - E_2 - E_3 + E_4) \quad C_Y = \frac{\pi}{16}(F_1 - F_2 - F_3 + F_4) \quad (1)(2)$$

$$S_X = \frac{\pi}{16}(E_1 + E_2 - E_3 - E_4) \quad S_Y = \frac{\pi}{16}(F_1 + F_2 - F_3 - F_4) \quad (3)(4)$$

The measured outputs from amplifiers 22, 23, 24, 25 attached to the I/Q demodulators 14 and 15 in FIG. 1 correspond to the real and imaginary parts of the complex quantities $D_x$ and $D_y$. The corresponding transmitted amplitudes A and B can be determined by Fourier analysis of the $D_x$ and $D_y$ measurements over at least one modulation cycle. The procedure involves numerically evaluating the following quantities.

$$\tan\psi = \frac{C_Y - S_X}{C_X - S_Y} \text{ or } \frac{C_Y - S_X}{C_X - S_Y} \quad A = \frac{2C_X}{\cos\psi} \quad B = \frac{2S_Y}{\cos\psi} \quad (5)(6)(7)$$

When a wood sample is present, new measurements of $D_x$ and $D_y$ are taken and new values of the quantities $C_x$, $C_y$, $S_x$, $S_y$ are evaluated using equations (3)–(4). The complex attenuations are then calculated using:

$$p = \frac{\frac{C_X}{A} + \frac{S_Y}{B}}{\cos\psi} \quad q = \frac{C_X}{A} - \frac{S_Y}{B} \quad r = -\frac{C_Y}{A} - \frac{S_X}{B} \quad (8)(9)(10)$$

$$\theta = 1/2(\psi - \arctan(r/q)) \quad u, v = p \pm (q^2 + r^2)^{1/2} \quad (11)(12)$$

Equations (3) onwards uniquely determine the grain angle θ within the range -90° to 90° and the principal phase shifts within a 360° range. The Fourier method has the advantage of providing good noise rejection, but it requires doing many arithmetic operations in the evaluations of equations (3)–(6). This calculation method choice does not depend on the waveform type used for the modulation.

In practice, the complex attenuations u and v determined from equation (12) are distorted by the effects of microwave reflection and refraction. These effects can be reduced by careful physical design, for example using sloping surfaces and microwave absorbers. The remaining distortions of the indicated attenuations will be consistent, and can be accounted for in the relationships used to identify wood properties from the indicated attenuations. Wood moisture content and specific gravity can be determined from statistical correlations based on the indicated principal attenuations and phase changes. Such evaluations of wood moisture content and specific gravity from principal attenuations and phase changes do not fall within the scope of the present invention.

A person skilled in the art can understand that the present invention can be realized in variant ways that differ from the specific descriptions given herein, and yet still remain within the spirit and scope of the invention. It is therefore to be understood that this invention includes all such variations that fall within its spirit and scope.

SIGNAL ACQUISITION AND PROCESSING

Depending on the actual hardware implementation, signal processing may be asynchronous or synchronous. In case of synchronous signal processing the acquisition of received signals is in-phase with the transmitter. In asynchronous signal processing, the transmitter runs independently from the receiver signal acquisition.

In asynchronous signal processing the field parameters are computed based on the transmitter and receivers signals not being synchronized. The synchronization is achieved by capturing both transmitter and receiver signals. Because of lack of synchronization the transmitter signals come with a random phase which has to be computed and used to adjust the material symmetry angle θ in equation 11.

Figure 3A:
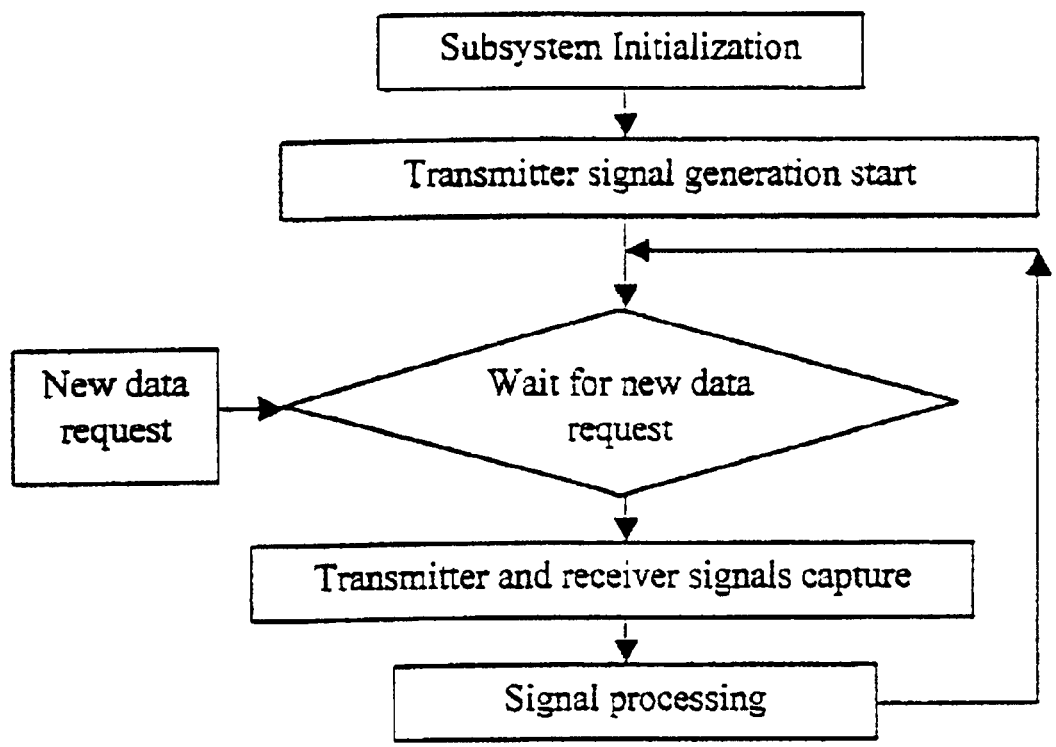
FIGS. 3a and 3b are flowcharts illustrating the steps of asynchronous signal processing.

The asynchronous signal processing include steps illustrated in the flowchart of FIG. 3a.

Subsystem initialization include miscellaneous tasks such as configuring analog-to-digital (A/D) and digital-to-analog (D/A) converters, and other system devices, pre-computing commonly used values, loading look-up tables, etc.

Next transmitter signal generation starts asynchronously to the data acquisition and continues throughout the entire subsystem operation. The transmitter signals are in the form of modulation periodic waveform, square-wave for example.

A/D converter waits for new data request typically from an encoder coupled with a board transfer system. Once a new data request is received both transmitter and receiver signals are acquired.

Signal processing follows equations (1) to (12).

In synchronous signal processing transmitter signal generation starts in sync with the receiver signal acquisition. Therefore there is no need to acquire and process transmitter signals. The advantage of this embodiment is simplified signal processing and less demand on A/D converter.

Figure 3B:
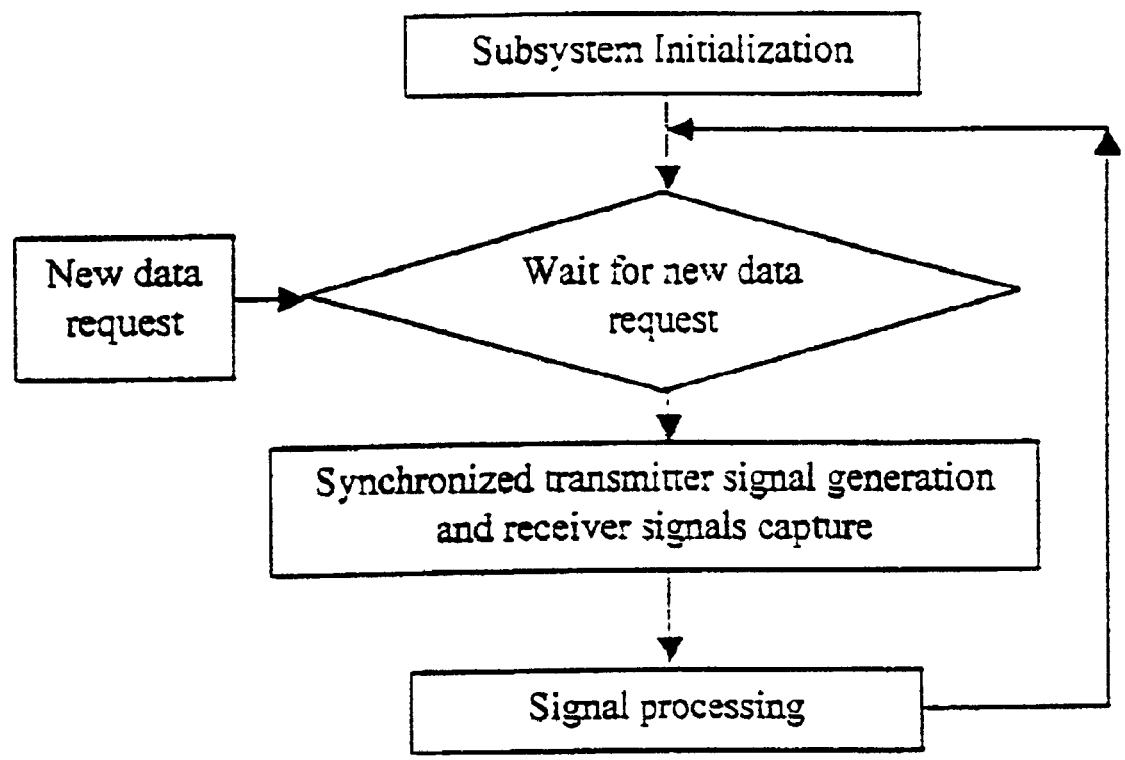

The synchronous signal processing include steps illustrated in the flowchart of FIG. 3b.

There are three types of calibration:

Reference (air) measurement,

Density calibration

Angle calibration

Reference (air) measurement consists of a measurement without any testing material (wood) present between transmitter and receiver. The signals are then processed and used for further computations of relative amplitudes and phases. Reference measurement "takes-off" effects of air, protective plates, and other sensor dependent factors on the attenuation and velocity of the microwave.

There are two ways reference measurement is applied: (a) at subsystem initialization and (b) during system operation, in-between boards. When subsystem is initialized, several reference measurements are taken and averaged to compute very accurate reference. Because of changes in temperature and other effects, this initial reference will need to be modified during system operation. To accomplish this, the subsystem takes reference measurements during the system run, in-between the actual testing specimens (boards). The space between adjacent boards is used for this purpose.

An additional purpose of the reference measurement is diagnostics of the subsystem operation. If the measurements are outside of an expected range of values for every sensor an error condition occurs.

Density calibration includes measurements of a homogeneous dielectric material of known properties. Typically 2 to 10 thickness steps are used. The results are used to modify models for density (D) and moisture content (MC) in a general form, $$D = f^D(u, v, T) \qquad (13)$$

$$MC = f^{MC}(u, v, T) \qquad (14)$$

$$MC = f^{MC}(u, v, D_{x\text{-}ray}, T) \qquad (15)$$

where T is temperature, $D_{x\text{-}ray}$ is density from an x-ray sub-system.

Angle calibration improves accuracy in detecting the angle of material symmetry for an anisotropic material. In the case of solid wood, that angle is equal to the grain angle θ (GA). This procedure includes collecting angular measurement using a rotating wire grid device. A rotating wire grid device consists of a set of parallel wires positioned in a plane perpendicular to the transmitting horn axis.

Then a relationship is established in a general form for every receiver $$GA = f^{GA}(\theta) \qquad (16)$$

This relationship is then used during system operation to correct angle measurements.

After the signal is collected and processed by the subsystem for the entire board, the data is further processed, including the following steps:

Board start/end adjustments

Filtering and smoothing

I/Q phase adjustment

Model computation

Board start/end adjustments eliminate the effect of the wave diffraction at the board ends, as the board enters and exits the sensor area. The material edges cause large oscillation in the field parameters. The procedure employed here includes elimination of these oscillations by applying a ramp-like (0 to 1) filter to the board ends, effectively eliminating the oscillations.

Filtering and smoothing is applied to the entire board to eliminate the effect of noise. A moving average, [1, 1, 1, 1, ...], or other type of filter may be used. For lumber products a typical length of a filter is 0.5 inch.

I/Q phase adjustment is necessary because of a narrow dynamic range of the I/Q phase detected, 360 degrees. Typically, a required phase range is up to 600 degrees. To insure stable measurements, the I/Q phase needs to be adjusted by +/−360*n. One of the solutions is using amplitude measurements to make adjustment decision. Amplitude and phase are generally related, the amplitude decreases and phase increases with the material density and moisture content. Therefore one may find a correct range of phase based on the amplitude measurement. One of the solution is using precompiled look-up-tables for limits of the phase adjustment.

Model computation is the last phase of the microwave data processing. It may involve (a) microwave only, (b) microwave and temperature, (c) microwave, density x-ray, and temperature, or (d) microwave and x-ray. Models for density, moisture content and grain angle are evaluated using equations (13) to (15).

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. In an apparatus for evaluating dielectrically-anisotropic materials wherein the apparatus has a plurality of microwave transmitters, the plurality of microwave transmitters having at least three different planes of polarization, each transmitter of the plurality of microwave transmitters for transmitting a microwave beam, and a plurality of microwave receivers with at least three different planes of polarization, wherein each transmitter of the plurality of microwave transmitters includes a means of modulating the transmitted microwave beam, the plurality of microwave transmitters and the plurality of microwave receivers arranged, relative to a workpiece to be measured, so as to cooperate in microwave communication therebetween and so as to irradiate the workpiece, and wherein connected to each receiver of the plurality of receivers is a means to identify the received amplitude and phase of a component of the transmitted microwave beam, and wherein connected to each receiver is a means for analyzing received signals of the transmitted microwave beam to thereby obtain at least three measurements including principal axes, attenuations and phase shifts of the received signals, and wherein said transmitters being at least a pair of transmitters modulated by modulation means for modulating using any two periodic functions, f(t) for a first transmitter of said transmitters and +/− $(1-(f(t))^2)^{1/2}$ for a second transmitter of said transmitters.

2. In an apparatus for evaluating dielectrically-anisotropic materials wherein the apparatus has a plurality of microwave transmitters, the plurality of microwave transmitters having differing planes of polarization, each transmitter of the plurality of microwave transmitters for transmitting a microwave beam, and a plurality of microwave receivers with differing planes of polarization, wherein the each transmitter of the plurality of microwave transmitters includes a means of modulating the transmitted microwave beam, the plurality of microwave transmitters and the plurality of microwave receivers arranged, relative to a workpiece to be measured, so as to cooperate in microwave communication therebetween and so as to irradiate the workpiece, and wherein connected to each receiver of the plurality of receivers is a means to identify the received amplitude and phase of a component of the transmitted microwave beam, and wherein connected to each receiver is a means for analyzing received signals of the transmitted microwave beam to identify principal axes, attenuations and phase shifts of the received signals, and wherein said transmitters being modulated by a signal corresponding to a nominal grain direction of said workpiece.

3. In an apparatus for evaluating dielectrically-anisotropic materials wherein the apparatus has a plurality of microwave transmitters, the plurality of microwave transmitters having at least three different planes of polarization, each transmitter of the plurality of microwave transmitters for transmitting a microwave beam, and a plurality of microwave receivers with at least three different planes of polarization, wherein the each transmitter of the plurality of microwave transmitters includes a means of modulating the transmitted microwave beam, the plurality of microwave transmitters and the plurality of microwave receivers arranged, relative to a workpiece to be measured, so as to cooperate in microwave communication therebetween and so as to irradiate the workpiece, and wherein connected to each receiver of the plurality of receivers is a means to identify the received amplitude and phase of a component of the transmitted microwave beam, and wherein connected to each receiver is a means for analyzing received signals of the transmitted microwave beam to thereby obtain at least three measurements including principal axes, attenuations and phase shifts of the received signals, and wherein said transmitters being modulated by a signal in random directions and having equal amplitudes.

4. In an apparatus for evaluating dielectrically-anisotropic materials wherein the apparatus has a plurality of microwave transmitters, the plurality of microwave transmitters having at least three different planes of polarization, each transmitter of the plurality of microwave transmitters for transmitting a microwave beam, and a plurality of microwave receivers with at least three different planes of polarization, wherein the each transmitter of the plurality of microwave transmitters includes a means of modulating the transmitted microwave beam, the plurality of microwave transmitters and the plurality of microwave receivers arranged, relative to a workpiece to be measured, so as to cooperate in microwave communication therebetween and so as to irradiate the workpiece, and wherein connected to each receiver of the plurality of receivers is a means to identify the received amplitude and phase of a component of the transmitted microwave beam, and wherein connected to each receiver is a means for analyzing received signals of the transmitted microwave beam to thereby obtain at least three measurements including principal axes, attenuations and phase shifts of the received signals, and wherein said microwave beam being a plurality of microwave beams for three dimensional scanning said workpiece in a plurality of scanning directions with respect to said workpiece.

5. The apparatus of claim 4 wherein said workpiece is dimensional lumber having flat surfaces and wherein said plurality of microwave beams are oriented angularly relative to said flat surfaces so as to be non-orthogonal to said flat surfaces.

* * * * *